United States Patent [19]

Parker

[11] 4,020,006

[45] Apr. 26, 1977

[54] FLUID CONTAINING DISPERSED PARTICLES SIMULATING LEUKOCYTES AND METHOD FOR PRODUCING SAME

[75] Inventor: James E. Parker, Long Beach, Calif.

[73] Assignee: ICL/Scientific, Fountain Valley, Calif.

[22] Filed: Aug. 14, 1975

[21] Appl. No.: 604,614

[52] U.S. Cl. .................. 252/408; 23/230 B; 424/2; 424/3; 424/93

[51] Int. Cl.² .................. G01N 33/16; G01N 1/30; C09K 3/00

[58] Field of Search ............ 252/408; 424/2, 3, 93; 23/230 B

[56] References Cited

UNITED STATES PATENTS

| | | | |
|---|---|---|---|
| 3,406,121 | 10/1968 | Jones | 252/408 |
| 3,412,037 | 11/1968 | Gochman et al. | 252/408 |
| 3,558,522 | 1/1971 | Louderback et al. | 252/408 |
| 3,574,137 | 4/1971 | Decasperis | 252/408 |
| 3,629,142 | 12/1971 | Marbach | 252/408 |
| 3,630,957 | 12/1971 | Rey et al. | 252/408 |
| 3,876,375 | 4/1975 | Maurukas | 252/408 |
| 3,901,655 | 8/1975 | Shukla | 252/408 |

*Primary Examiner*—Benjamin R. Padgett
*Assistant Examiner*—T. S. Gron
*Attorney, Agent, or Firm*—Fulwider, Patton, Rieber, Lee & Utecht

[57] ABSTRACT

Microspores derived from flowering plants are dispersed in fluids to simulate leukocytes. Reconstituted body fluids utilized as standards in clinical examination of fluids such as urine contain a known quantity of microspores to simulate leukocytes when examined under a high power field. Microspores utilized to simulate leukocytes have a particle size of between 10 microns and 25 microns and are stained utilizing the same stains and techniques utilized for staining leukocytes. Microspores derived from the Paper Mulberry tree are highly preferred for use as leukocyte resembling particles.

11 Claims, No Drawings

FLUID CONTAINING DISPERSED PARTICLES SIMULATING LEUKOCYTES AND METHOD FOR PRODUCING SAME

BACKGROUND OF THE INVENTION

This invention relates to reconstituted body fluids having leukocyte simulating particles dispersed therein and a method for producing same.

In carrying out the clinical examination of various body fluids, such as for example, blood, urine, spinal fluid and the like, it is standard practice to utilize a known sample of the body fluid as a standard for determining the quantity of the constituent being tested for and for quality control purposes to test the accuracy of the procedure. For this purpose standard body fluid samples containing precise levels of key constituents are prepared on a commercial basis. For the purpose of increasing the stability and shelf life, the commercially available standard body fluids are normally supplied in the lyophilized form and are reconstituted by the addition of water immediately prior to use. Accordingly such commercially prepared standard fluids are referred to herein as reconstituted body fluids.

An important constituent of body fluids insofar as diagnostic techniques are concerned are white cells or leukocytes. Depending on the particular body fluid being examined, the presence or absence of leukocytes and the number of leukocytes if present provide important diagnostic information on the condition of the patient and a standard sample of body fluid should advantageously include a known value of leukocytes.

Leukocytes, however, have a relatively short life in vitro, normally on the order of 18 to 30 hours. Consequently, in the commercially available reconstituted body fluids, known amounts of particles are introduced as a substitute for the leukocytes which, as mentioned before, have a relatively short in vitro existence. Such particles have included polystyrene latex spheres, butadiene spheres, polyvinyltuoluene spheres, silica, kaolin and the like which are prepared to particle size so as to resemble a leukocyte. Such particles, however, are readily distinguished from leukocytes and, accordingly, reconstituted body fluids utilizing such particles in the place of leukocytes are readily detected by the technician and detract from the use of the body fluid as a hidden sample for quality control purposes. In addition, such particles resemble leukocytes in size only but not in appearance and therefor detract from the use of the reconstituted body fluid as a teaching tool to aid new technicians in recognizing leukocytes in body fluids.

The reconstituted body fluids of the present invention overcome the foregoing deficiencies in prior art reconstituted fluids and therefore, are advantageously utilized both as a quality control tool in the clinical examination of body fluids and as a teaching vehicle to aid new technicians in the handling and recognition of leukocytes in body fluids.

SUMMARY OF THE INVENTION

The present invention provides a reconstituted fluid in which are dispersed particles which unexpectedly resemble leukocytes in size, appearance and staining characteristics. The leukocyte simulating particles introduced in accordance with the method of this invention detract in no way from the chemical and physiological characteristics of the reconstituted body fluids of the present invention.

More particularly, the leukocyte simulating particles are vegetable originated particles, which when stained with conventional biological staining materials reveal a defined nucleus and cytoplasm and closely resemble leukocytes as they would appear after staining in a body fluid. The particles are microspores produced during the reproductive cycle of certain plants and are more commonly referred to as the pollen of the plant. These particles are of a size range of between about 12 microns and about 25 microns and when contacted with the biological stain utilized to stain leukocytes, reveal a nucleus and cytoplasm closely resembling the appearance of leukocytes.

The reconstituted body fluids of the present invention are prepared by lyophilizing body fluids, for example, urine, blood serum, spinal fluid, and the like to which known amounts of particular chemical constituents have been added. The particles of the present invention may be introduced prior to or immediately following lyophilization of the body fluid or may be subsequently introduced at the time of reconstitution of the lyophilized fluid. As utilized herein, the term "reconstituted" as applied to body fluids is intended to denominate those fluids which have been lyophilized so that they may be stored for extended periods of time without deterioration of the chemical composition thereof and which are combined with a liquid phase, predominately water, prior to their use as a standard solution or as a teaching tool and the like.

Although the following detailed description is confined to the case where the reconstituted fluid is urine, it should be clear that the present invention encompasses other reconstituted body fluids in which it is desired to provide a known amount of particles resembling leukocytes. Thus, other body fluids such as blood serum, plasma, spinal fluid and joint fluid are reconstituted for diagnostic or other purposes.

Other advantages of the present invention will become apparent from the following detailed description and claims appended hereto.

DETAILED DESCRIPTION OF THE INVENTION

In accordance with the present invention, the microspores or pollen produced by certain plants and fungi during their reproductive cycle have been found to closely resemble the appearance of leukocytes when dispersed in a fluid. These particles, when stained, develop the same color for the nucleus and cytoplasm as is developed when leukocytes are stained and accordingly, when viewed through a microscope, are very difficult to distinguish from actual leukocytes. In addition, the particles are selected within the range of particle size of normal leukocytes and have been found to have substantially the same sedimentation rate so that when dispersed in fluid they resemble leukocytes in size, appearance and other physical attributes.

Although not specifically limited thereto, the microspores are preferably derived from the pollen of the paper mulberry tree, *Broussonetia papyrifera;* white mulberry, *Morus albus;* the pecan, *Carya illinoensis;* ragweed, *Ambrosia;* and spores of basidiomycetous fungi, such as for example, of the family Lycoporaceae. The microspores of the aforementioned plants are highly preferred for use in the present invention because they are of a particle size ranging between about 12 microns and 25 microns which is the particle size range of leukocytes and thus require a minimum of screening or particle size selection procedures for use in the present invention. However, the pollens of other plants are also useful in the present invention provided they are of the aforementioned particle size range. Plant microspores which are larger or smaller in particle size than the leukocytes range are, of course, not suitable for the present invention as they will not appear as leukocytes when examined under the microscope. In addition microspores outside the particle size range of leukocytes will have sedimentation rates somewhat different than leukocytes which may result in inaccurate particle values when examining the reconstituted fluid using conventional technique.

Another important feature with respect to the use of plant microspores is that they take a stain in substantially the same manner as leukocytes so that after staining the microspores strongly resemble leukocytes having defined nucleus and cytoplasm visible when viewed through a microscope. The staining technique for the microspores in reconstituted body fluids is the same as is utilized for the staining of actual leukocytes in body fluids. Staining composition conventionally used for the staining of leukocytes in body fluids are equally effective in the reconstituted body fluids of this invention. For example, mixtures of eosin (Acid Red 87; CI 45,380) and methyl blue (Acid Blue 93; CI 42, 708) when combined in various proportions and solvents such as to form Romanowski's stain, Wright's stain, Lieshman's stain and the like are highly effective in staining the reconstituted body fluids of this invention. This feature is highly important when utilizing reconstituted body fluid as a quality control device since no special or different techniques are required than would be utilized for the examination of body fluids, and thus, samples of the reconstituted body fluid produced in accordance with this invention can be "hidden" among patent derived samples to provide a check on the accuracy of the testing procedures.

In producing a reconstituted body fluid, in accordance with the present invention, the body fluid is obtained from a "pool" of normal body fluid derived from healthy patients as is conventional in the art. The fluid is assayed for certain constitutents; in the case of urine for protein, hemoglobin, glucose and ketone bodies which are the constitutents determined in a routine urinalysis. As is also conventional the fluid is filtered to remove particular matter and constituents are added to raise their value in the fluid to a known, predetermined level. The fluid is lyophilized by vacuum freeze drying to remove the liquid portion and reconstituted prior to use by the addition of water.

The microspores are introduced prior to or subsequent to lyophilization of the body fluid and can be incorporated in the lyophilized solids or can be incorporated in the reconstituting liquid. For most testing purposes a sufficient quantity of microspores are introduced to provide a count of between 1 to about 100 cells under a high power field (430X), although the concentration of microspores can be varied widely depending upon the type of body fluid being reconstituted and type of abnormality for which the fluid is to be examined.

The following example illustrates the use of plant originated microspores in the preparation of a reconstituted urine sample.

EXAMPLE

A reconstituted urine sample was prepared to the following assay:

| Constituent | Value Range |
|---|---|
| Appearance | Slightly turbid |
| Color | Yellow |
| Specific Gravity | 1.020 – 1.022 |
| pH | 5.6 – 5.8 |
| Protein | 350 – 400 mg% |
| Glucose | 480 – 560 mg% |
| Ketone Bodies[1] | 8 – 12 mg% |
| Blood (hemoglobin) | 7.3 – 8.5 mg% |
| Red Blood Cells (stabilized)[2] | 8 – 12/hpf[3] |
| Leukocytes (Plant derived microspores) | 20 30/hpf[3] |

[1]Reported as mg% of acetoacetic acid.
[2]Red blood cells stabilized with tannic acid.
[3]Hpf; high power field at 430X.

60 ml of assayed urine was obtained from a urine pool comprising normally healthy human urine. The urine was subjected to a series of filtering steps down to a final filter of 4 microns to remove all sedimentation. Sufficient proportions of protein, glucose, ketone and hemoglobin were added to bring the assay of the urine to the foregoing final assay. The sample was lyophilized by vacuum freeze drying to remove the liquid therefrom and sealed in a sterile container.

To 1 liter of sterilized water was added .4 gms of stabilized red blood cells and 1 gm of microspores having a particle size of between about 12 and about 25 microns. The red blood cells were stabilized in the conventional manner with tannic acid to prevent degradation during prolonged storage periods as is standard practice.

The microspores were supplied by Duke Standards Co. of Palo Alto, Calif. and were collected from the blooms of the Paper Mulberry tree (*Broussonetia papyrifera*). The microspores had been screened to remove gross impurities such as leaves, stalks, dirt and the like and had been dewaxed by solvent washing.

The sterilized water containing the red blood cells and microspheres was agitated to throughly disperse the particles throughout and a 1 micro liter sample was extracted and examined under high power field for the red blood cell value and the microsphere value. The values are adjusted, if necessary, by the addition of more sterilized water to lower the values or additional particles to raise the values. The ph of the water was adjusted to 5.6 to 5.8 and buffered with a citric acid buffer. 60 mls of the thoroughly agitated water were removed and placed in a sterilized sealed container. Both the liquid portion and the lyophilized urine portion can be stored for periods up to one year at a temperature of between 2° C and 8° C.

The urine sample was reconstituted by mixing the contents of the two bottles and after allowing the reconstituted urine to achieve room temperature, the urine sample was analyzed by conventional clinical techniques. In particular, one drop of the reconstituted urine was placed on a microscope slide and contacted with a stain consisting of Crystal violet (Basic Violet 3: CI 42555)Safranin-O(Basic Red 2; CI 50,240) in vehicle of ammonium oxalate methanol, as supplied by ICL Scientific, Fountain Valley, Calif. When examined under high power field, the microspores had developed a blue nucleus and a reddish cytoplasm surrounding the nucleus and thus appeared as actual leukocytes would appear in a urine sample when stained with the same composition. The microspores resembled leukocytes so closely that only a highly trained observer could readily distinguish that the microspores were not leukocytes. The presence of the microspores had no ascertainable adverse effects on the reconstituted sample nor were the analytical or clincial techniques utilized to test the sample altered in any way.

In the foregoing example the microspores were introduced and maintained in the liquid portion prior to the reconstitution thereof by intermixing the lyophilized portion and the liquid portion. However, the microspores can be added to the urine prior to lyophilization or immediately thereafter with no adverse effects on the microspores or the reconstituted fluid.

While the example relates to a reconstituted urine sample it should be clear that the microspores are equally effective in the preparation of other types of body fluids for clinical work, such as, for example, reconstituted blood serum and reconstituted spinal fluid. In both of these types of body fluids, standard reconstituted samples are normally run along with actual test samples to insure accuracy and standardization of the testing procedures. The presence or absence of white blood cells and the number of cells in these fluids also provides an important diagnostic clue to a physician as to a patient's condition. Accordingly, it is important that the standard samples include known amounts of particles resembling leukocytes as a standard for the technician and also as a quality control test to insure the accuracy of the technician's procedures.

I claim:

1. In a method for preparing a standard body fluid for use as a control in clinical testing comprising the steps of introducing materials into a body fluid to bring the proportion of constituent components to a predetermined level followed by lyophilization to remove the liquid phase therefrom and adding liquid to reconstitute the lyophilized sample prior to its use, the improvement comprising:
   introducing into said standard body fluid a predetermined amount of particles simulating leukocytes, said particles consisting of the microspores of plants selected from the group consisting of *Broussonetia papyrifera*, *Morus albus* and *Carya illinoensis*, said microspores having a particle size ranging between about 10 microns and about 25 microns and being reactive with a biological tissue staining compound for staining leukocytes to reveal a defined nucleus and cytoplasm.

2. The method of claim 1 wherein said body fluid is urine and said microspores are added in an amount sufficient to provide a value of between about 1 and about 100 microspores under high power field at 430X.

3. The method as defined in claim 1 wherein said microspores are dispersed in said liquid utilized for reconstituting the body fluid.

4. The method as defined in claim 1 wherein said microspores are introduced into the body fluid prior to the lyophilization step.

5. The method as defined in claim 1 wherein said microspores are introduced into the lyophilized portion prior to the reconstitution step.

6. A preparation for use in forming a reconstituted body fluid standard for use as a control in clinical testing, said preparation consisting of a body fluid in the anhydrous form having predetermined constituent amounts and a predetermined amount of a plurality of plant microspores having a particle size of between 10 and 25 microns, said microspores being selected from the group consisting of *Broussonetia papyrifera*, *Morus albus* and *Carya illinoensis*, said microspores resembling leukocytes and revealing a nucleus and cytoplasm when contacted with a leukocyte staining compound.

7. The preparation of claim 6 wherein said body fluid is urine.

8. A method for preparing a dispersion comprising artifical leukocytes, for use as a control in clinical testing, said method comprising:
   introducing into a body fluid having predetermined constituent amounts, a predetermined amount of particles consisting of plant originated microspores derived from *Broussonetia papyrifera*, said particles having a size ranging from between 10 microns and 25 microns and displaying a nucleus and cytoplasm when contacted with a leukocyte staining compound.

9. The method as defined in claim 8 wherein said body fluid is a reconstituted body fluid selected from the group consisting of urine, blood serum, plasma, spinal fluid and joint fluid.

10. The method as defined in claim 8 wherein said body fluid comprises a reconstituted body fluid and said particles are dispersed therein in an amount sufficient to provide a predetermined value when examined under a high power field.

11. The method as defined in claim 8 wherein said body fluid is reconstituted urine.

* * * * *